United States Patent
Keating et al.

(10) Patent No.: US 7,301,067 B2
(45) Date of Patent: Nov. 27, 2007

(54) MICE WHICH ARE +/− OR −/− FOR THE ELASTIN GENE AS MODELS FOR VASCULAR DISEASE

(75) Inventors: Mark T. Keating, Chestnut Hill, MA (US); Dean Y. Li, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 125 days.

(21) Appl. No.: 11/046,006

(22) Filed: Jan. 28, 2005

(65) Prior Publication Data

US 2005/0223419 A1    Oct. 6, 2005

Related U.S. Application Data

(63) Continuation of application No. 09/258,217, filed on Feb. 26, 1999, now Pat. No. 6,903,244.

(51) Int. Cl.
| | |
|---|---|
| *G01N 33/00* | (2006.01) |
| *G01N 33/567* | (2006.01) |
| *C12Q 1/00* | (2006.01) |
| *A61K 38/00* | (2006.01) |
| *C07K 1/00* | (2006.01) |

(52) U.S. Cl. ............... 800/3; 800/18; 435/4; 435/7.21; 530/300; 530/350
(58) Field of Classification Search ............ 435/4, 435/7.21; 514/2; 530/300, 350; 800/3, 800/18

See application file for complete search history.

(56) References Cited

OTHER PUBLICATIONS

Leonard et al., 1995, Immunological Reviews, vol. 148, pp. 97-114.*
Houdebine, L-M., 2002, Journal of Biotechnology, vol. 98, p. 145-160.*
Mogil et al., 1999, Pain, vol. 80, pp. 67-82.*
Sigmund, C., Jun. 2000, Arterioscler. Thromb. Vasc. Biol., p. 1425-1429.*
Bum, J. and Goodship, J., "Developmental genetics of the heart", Curr. Opin. Genet. Dev., (Jun. 1996) 6(3):322-325.
Keating, M.T., "On the trail of genetic culprits in Williams syndrome", Cardiovasc. Res., (1997) 36:134-137.
Li, D.Y., et al., "Elastin is an essential determinant of arterial morphogenesis", Nature, (May 21, 1998).
Li, D.Y., et al., "Elastin point mutations cause an obstructive vascular disease, supravalvular aortic stenosis", Hum. Mol. Genet., (1997) 6(7):1021-1028.
Li, D.Y., et al., "Novel Arterial Pathology in Mice and Humans Hemizygous for Elastin", J. Clin. Invest., (Nov. 1998) 102(10):1783-1787.
Perrin, S. and Foster, J., "Developmental Regulation of Elastin Gene Expression", Crit. Rev. Eukaryot. Gene Expr., (1997) 7(1&2):1-10.
Rabinovitch, M., "Cell-Extracellular Matrix Interactions in the Ductus Arteriosus and Perinatal Pulmonary Circulation", Semin. Perinatol., (Dec. 1996) 20(6):531-541.
Sauvage, M., et al., "Aortic Elastin and Collagen Content and Synthesis in Two Strains of Rats with Different Susceptibilities to Rupture of the Internal Elastic Lamina", J. Vasc. Res., (1997) 34:126-136.
Tassabehji, M., et al., "An elastin gene mutation producing abnormal tropoelastin and abnormal elastic fibres in a patient with autosomal dominant cutis laxa", Hum. Mol. Genet., (1998) 7(6):1021-1028.
Tassabehji, M., et al., "Elastin: genomic structure and point mutations in patients with supravalvular aortic stenosis", Hum. Mol. Genet., (1997) 6(7):1029-1036.
Wu, Y.-Q., et al., "Delineation of the Common Critical Region in Williams Syndrome and Clinical Correlation of Growth, Heart Defects, Ethnicity, and Parental Origin", Am. J. Med. Genet.(1998) 78:82-89.
Yamamoto, M., et al., "Increase in Elastin Gene Expression and Protein Synthesis in Arterial Smooth Muscle Cells Derived From Patients with Moyamoya Disease", Stroke, (Sep. 1997) 28(9): 1733-1738.
Anders, et al., "Murine Models of Renal Disease: Possibilities and Problems in Studies Using Mutant Mice", Exp. Nephrol., vol. 8, pp. 181-193 (2000).
Bradley et al., "Modifying the Mouse: Design and Desire", Biotechnology, vol. 10, pp. 534-539 (May 1992).
Louis-Marie Houdebine, J. Biotechnology, 34, pp. 269-287 (1994).
Morris, "Genetic aspects of supravlvular aortic stenosis", Current Opinion in Cardiology, vol. 13, pp. 214-219 (1998).
Murayama et al., Am. J. Physiol., vol. 261 (6, pt. 2), H1716-H1726 (1991).
Palmiter et al., Science, vol. 222, pp. 809-814 (1983).
Pursel et al., J. Reprod. Fert., Suppl. 40, pp. 235-245 (1990).
R.F. Seamark, Reprod. Fertil. Dev., vol. 6, pp. 653-657 (1994).
Reitamo et al., Biological Kournal, vol. 302 (pt2), pp. 331-333 (1994).
Sechler et al., Ciba Foundation Symposium, vol. 192, pp. 148-171 (1995).
Wu et al., Methods in Gene Biotechnology, Chapter 17, pp. 339-365 (1997).
Wydner et al., Genomics, vol. 23, pp. 125-131 (1994).

* cited by examiner

Primary Examiner—Shin-Lin Chen
(74) Attorney, Agent, or Firm—Ropes & Gray LLP (57) ABSTRACT

Elastin, the main component of arterial extracellular matrix, was thought to have a purely structural role. Consistent with this view, elastin hemizygous mice maintain arterial extensibility by increasing the number of elastic lamellae during development. However, mice lacking elastin die of obstructive arterial pathology. This pathology results from subendothelial proliferation and reorganization of smooth muscle, cellular changes similar to those observed in atherosclerosis. Thus, elastin is a molecular determinant of arterial morphogenesis and likely plays a central role in vascular disease. Mice which are heterozygous and null for the elastin gene have been developed. These mice are extremely useful for screening for drugs useful for treating persons with atherosclerosis, hypertension, SVAS or other vascular diseases.

6 Claims, 5 Drawing Sheets

MICE WHICH ARE +/− OR −/− FOR THE ELASTIN GENE AS MODELS FOR VASCULAR DISEASE

The present application is a continuation of and claims priority to U.S. application Ser. No. 09/258,217, filed Feb. 26, 1999 now U.S. Pat No. 6,903,244, the specification of which is hereby incorporated by reference in its entirety.

This application was made with Government support under an NIH grant (Grant No. NIHK08HL03490-03) funded by the National Institutes of Health, Bethesda, Md. The U.S. Government has certain rights in this invention.

BACKGROUND OF THE INVENTION

Vasculogenesis begins early in vertebrate development and culminates in the formation of a complex network of arteries, veins, and capillaries. Once formed, the gross and microscopic structure of this network is stable unless disrupted by disease. Genetic and cell culture studies have begun to identify molecular determinants of vasculogenesis, and these determinants have defined three distinct stages of vascular development (Hanahan, 1997; Folkman and D'Amore, 1996). In the first stage, splanchnic mesoderm coalesces to form simple tubes of endothelial cells. Vascular endothelial growth factor defines this stage (Shalaby et al., 1995; Fong et al., 1995; Carmeliet et al., 1996). The second stage involves the recruitment of mesenchymal cells by the endothelium, a process coordinated by angiopoietin and platelet-derived growth factor (Ferrara et al., 1996; Suri et al., 1996; Lindahl et al., 1997; Sato et al., 1995). In the third stage, mesenchyme differentiates into smooth muscle and extracellular matrix deposition begins. Transforming growth factor beta has been implicated in this stage (Folkman and D'Amore, 1996; Beck and D'Amore, 1997). After the third stage of vascular development, arterial smooth muscle cells exit the cell cycle and vascular structure is stabilized (Schwartz et al., 1990; Owens, 1995; Glukhova et al., 1991). The molecular determinants of this final stage are unknown.

There is growing evidence that the extracellular matrix regulates cellular function during organogenesis. Fibronectin, vitronectin, collagen, and other extracellular matrix proteins bind to integrins on the surface of cells (Gumbiner, 1996; Hynes, 1992), providing morphogenic signals that regulate cell proliferation, migration, and differentiation (Adams and Watt, 1993; Hynes, 1994). Disruption of fibronectin in mice causes dramatic developmental abnormalities, including failure to develop a notochord and somites (George et al., 1993). Null mutations in genes encoding fibronectin receptors, or integrins, lead to embryonic or perinatal death from developmental abnormalities resembling those observed in mice lacking fibronectin (Yang et al., 1993; Yang et al., 1995). Not all cell-matrix interactions, however, are necessary for normal morphogenesis. For example, disruption of vitronectin, tenascin C, and integrin alpha 1 have no apparent effect on development (Zheng et al., 1995; Saga et al., 1992; Gardner et al., 1996).

Elastin is the dominant arterial extracellular matrix protein (Parks et al., 1993). This protein is encoded by a single gene, and organized into polymers that form concentric rings of elastic lamellae around the arterial lumen. Each elastic lamella alternates with a ring of smooth muscle, forming a lamellar unit. The function of elastic fibers was thought to be purely structural, providing tensile strength and resiliency to the aorta and other arteries. Because of its structural role, investigators believed that disruption of elastin would lead to dissection of arteries. This view was supported by studies associating decreased elastin content and increased elastase activity with arterial aneurysms in humans and other species (Thompson, 1996; Terpin and Roach, 1987). In addition, disruption of collagen I and fibrillin, prominent arterial extracellular matrix proteins, resulted in rupture of blood vessels in mice and humans (Lohler et al., 1984; Dietz and Pyeritz, 1995). Our human molecular genetic studies demonstrated, however, that ELN mutations do not cause arterial dilatation, but instead cause an obstructive arterial disease, supravalvular aortic stenosis (SVAS) (Curran et al., 1993; Ewart et al., 1993). To define the role of ELN in arterial development and disease, we generated mice hemizygous (ELN +/−) and homozygous (ELN −/−) for an ELN null mutation. From characterization of these mice, we conclude that elastin has two distinct functions. One is to provide arterial elasticity and ameliorate wall stress. A second is to control smooth muscle proliferation and organization during late arterial development. Elastin, therefore, is a molecular determinant of arterial morphogenesis, defining a fourth stage of development, the stage of arterial stabilization.

The publications and other materials used herein to illuminate the background of the invention or provide additional details respecting the practice, are incorporated by reference, and for convenience are respectively grouped in the appended List of References.

SUMMARY OF THE INVENTION

Elastin, the main component of the extracellular matrix of arteries, was thought to have a purely structural role (Parks et al., 1993). Disruption of elastin was believed to lead to dissection of arteries (Thompson, 1996; Terpin and Roach, 1987), but we showed that mutations in one allele encoding elastin cause a human disease in which arteries are blocked, namely, supravalvular aortic stenosis (Curran et al., 1993; Ewart et al., 1993). Here we define the role of elastin in arterial development and disease by generating mice that lack elastin. These mice die of an obstructive arterial disease, which results from subendothelial cell proliferation and reorganization of smooth muscle. These cellular changes are similar to those seen in atherosclerosis. However, lack of elastin is not associated with endothelial damage, thrombosis or inflammation, which occur in models of atherosclerosis. Hemodynamic stress is not associated with arterial obstruction in these mice either, as the disease still occurred in arteries that were isolated in organ culture and therefore not subject to hemodynamic stress. Disruption of elastin is enough to induce subendothelial proliferation of smooth muscle and contributes to obstructive arterial disease. Thus, elastin has an unanticipated regulatory function during arterial development, controlling proliferation of smooth muscle and stabilizing arterial structure.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIGS. 2A-H show the histology of different developmental stages in ELN+/+ and ELN −/− aortas. Cross-sections of ascending aortas (at the level of the pulmonary artery) stained with hematoxylin and eosin were examined at E15.5 (FIGS. 2A and 2B), E17.5 (FIGS. 2C and 2D), P0.5 (FIGS. 2E and 2F) and P2.5 (FIGS. 2G and 2H). No difference was noted at E15.5. Subsequent timepoints revealed subendothelial accumulation of cells in ELN−/− mice (arrows) and obliteration of the lumen by P2.5. All ELN −/− mice were dead by P4.5, presumably from the rapid obliteration of the aorta and other arteries. The ratios of lung weight to body weight and of heart weight to body weight in ELN −/− and ELN +/+ mice were comparable, suggesting that pulmonary edema was not the cause of death (n=8). There was no evidence of cardiac hypertrophy, dilatation or ischemia.

FIGS. 3A-H show the consequences of elastin deficiency in different arteries. Sections of pulmonary arterioles (arrow) at the level of a terminal bronchiole at P2.5 (FIGS. 3A and 3B), the internal mammary artery (arrow) at P2.5 (FIGS. 3C and 3D), a distal portion of the subclavian artery at P0.5 (FIGS. 3E and 3F), and the abdominal aorta at P0.5 (FIGS. 3G and 3H) were stained with hematoxylin and eosin and examined. There is increased cellularity and narrowing of the lumen for all of these ELN −/− arteries.

FIGS. 4A-J show the mechanism of luminal obliteration in ELN −/− mice. FIGS. 4A and 4B show sections of mice at P0.5 immunostained with antisera against smooth muscle α-actin. The subendothelial cells in ELN −/− mice stained positively (arrow), indicating that they were smooth muscle. FIGS. 2C and 2D show sagittal sections of the ascending aorta at P2.5, stained with hematoxylin and eosin. The subendothelial cells in ELN −/− mice were longitudinally oriented (arrow), whereas normal orientation is circumferential. FIGS. 4E and 4F show aortic sections of E17.5 mice immunostained with antisera against PCNA (dark brown nuclei). The percentage of cells stained with PCNA was greater in ELN −/− mice than in ELN +/+ mice (88% vs. 35%), indicating increased cell proliferation in ELN −/− aortas. FIGS. 4G and 4H show sections of mice at P0.5 immunostained with antisera against von Willebrand factor (red). There was no evidence of endothelial damage. FIGS. 4I and 4J are sections of mice at P0.5 incubated with Masson trichrome, which stains collagen green. There was no collagen deposition.

FIGS. 5A-G show the results of organ culture of ELN +/+ and ELN −/− aortas. Cross-sections of ELN +/+ (FIGS. 5A, 5C and 5E) and ELN −/− (FIGS. 5B, 5D and 5F) aortas with no incubation (FIGS. 5A and 5B) and 24 hours of incubation (FIGS. 5C, 5D, 5E and 5F) in DMEM plus 5% fetal bovine serum. Sections in FIGS. 5A-5D were stained with antisera against smooth muscle α-actin whereas sections in FIGS. 5E-5F were stained with hematoxylin and eosin. FIGS. 5D and 5F show obliteration of the ELN −/− aortas occurs after 24 hours of incubation. FIG. 5G shows a comparison of in vivo and in vitro proliferative indices. The proliferative indices of ELN +/+ and ELN −/− aortas in organ culture (E16.5, 24 hours incubation; n=8) were comparable to those obtained in vivo (E15.5-E17.5; n=5).

DETAILED DESCRIPTION OF THE INVENTION

A) Targeted Disruption of Murine ELN

Figure 1:
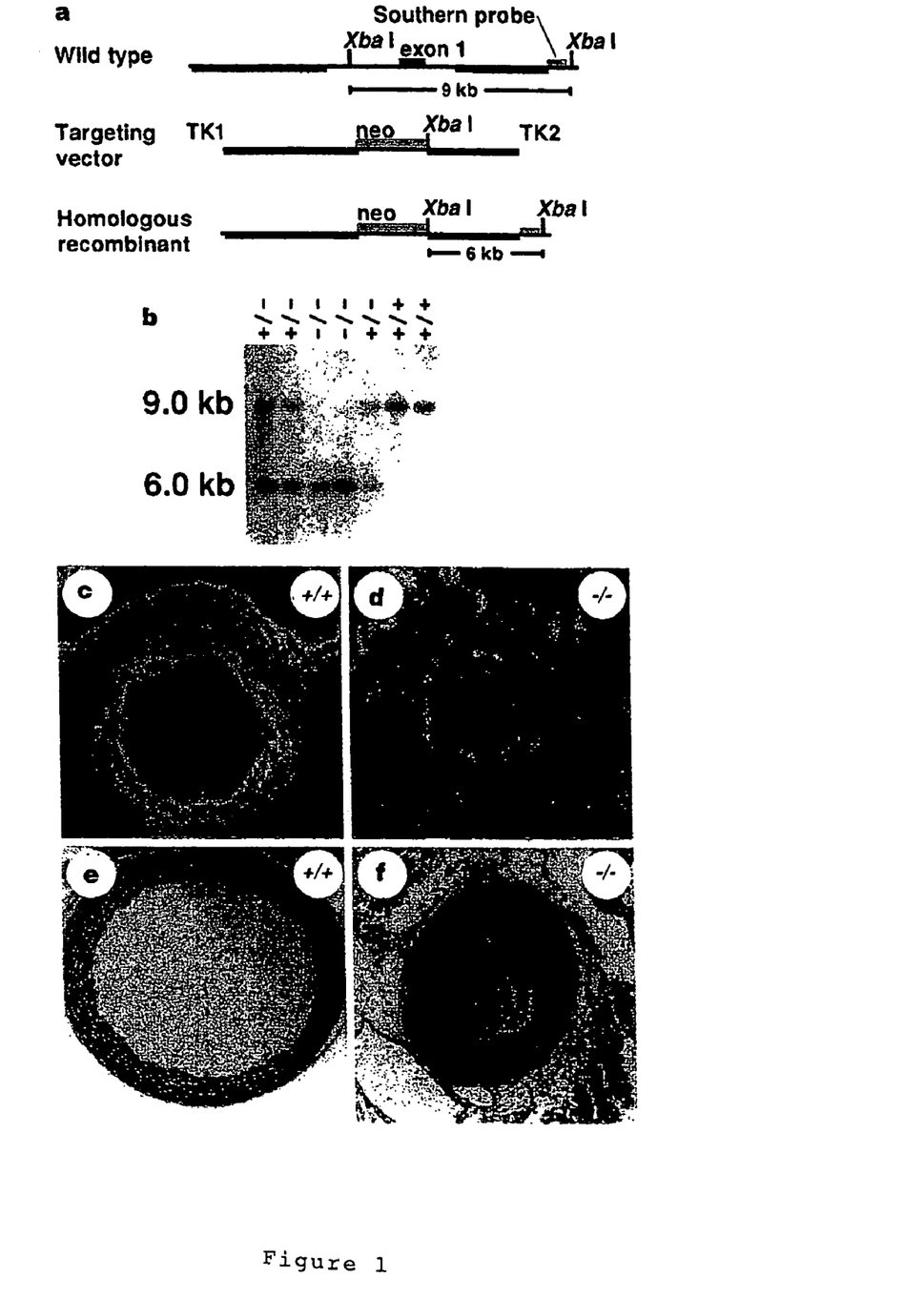
FIG. 1A is a diagram of the targeting vector designed to delete the promoter and exon 1 of the ELN gene. TK is thymidine kinase.
FIG. 1B shows a Southern blot analysis of tail DNA, digested with XbaI, from ELN+/+, ELN +/−, and ELN −/− mice. The 9 kb wild-type and 6 kb targeted XbaI fragments were identified using a probe outside the 3' region of homology.
FIGS. 1C and 1D show in situ hybridization of ELN +/+ (FIG. 1C) and ELN −/− (FIG. 1D) mice at E17.5 used to study ELN expression. Dark-field photomicrographs show the presence of silver grains in ELN +/+ mice and their absence in ELN −/− mice. The results demonstrate that no ELN mRNA is detected in ELN −/− mice.
FIGS. 1E and 1F show that Hart stain detected elastic fibers (stained dark brown) in ascending aortas from ELN+/+ mice (FIG. 1E) at birth (post partum 0.5 day). Elastin is organized into polymers that form concentric rings of elastic lamella around the arterial lumen. Each elastic lamella alternates with a ring of smooth muscle, forming a lamellar unit. There were no elastic fibers in ELN −/− mice (FIG. 1F).
Figure 2:
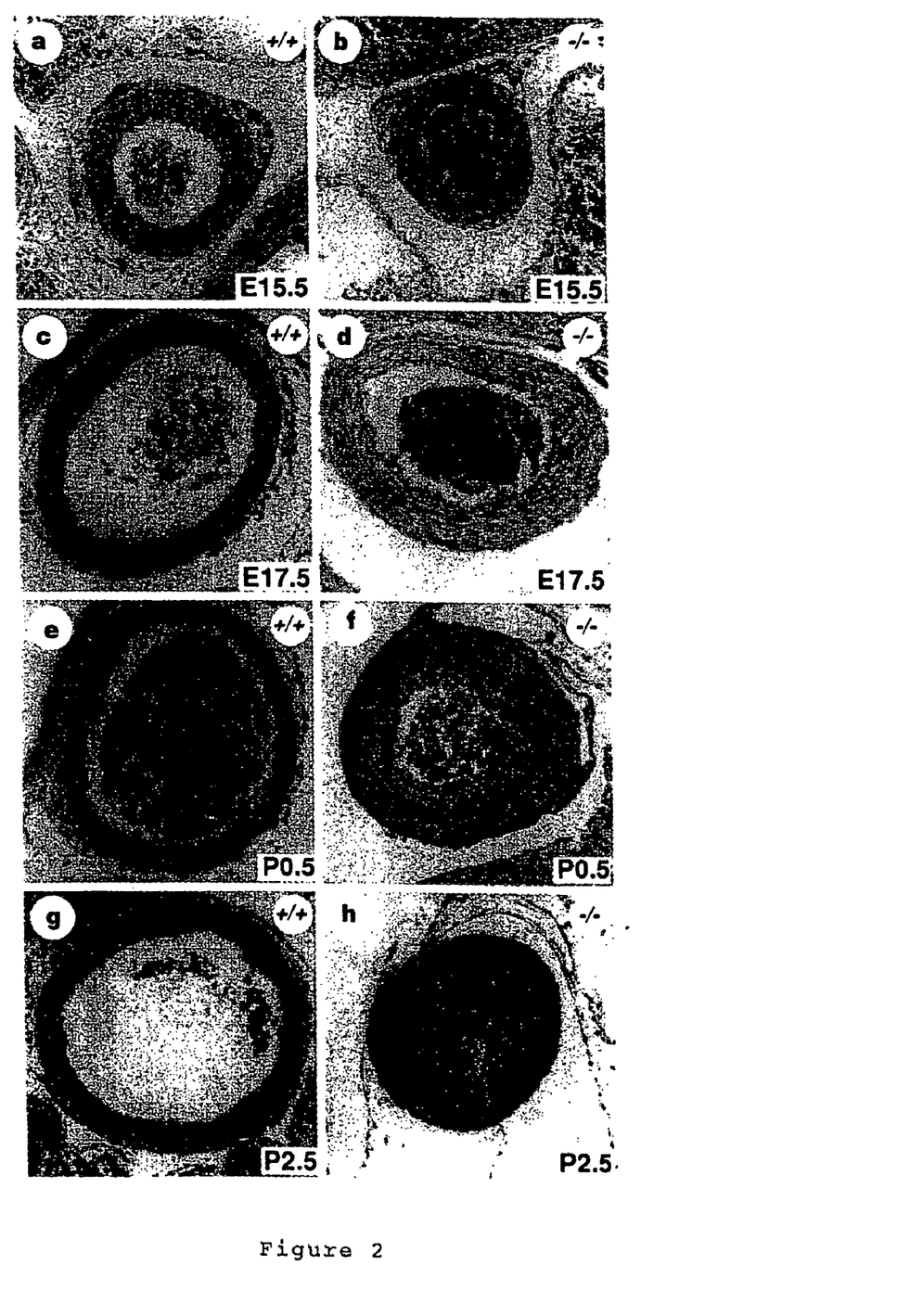
Figure 3:
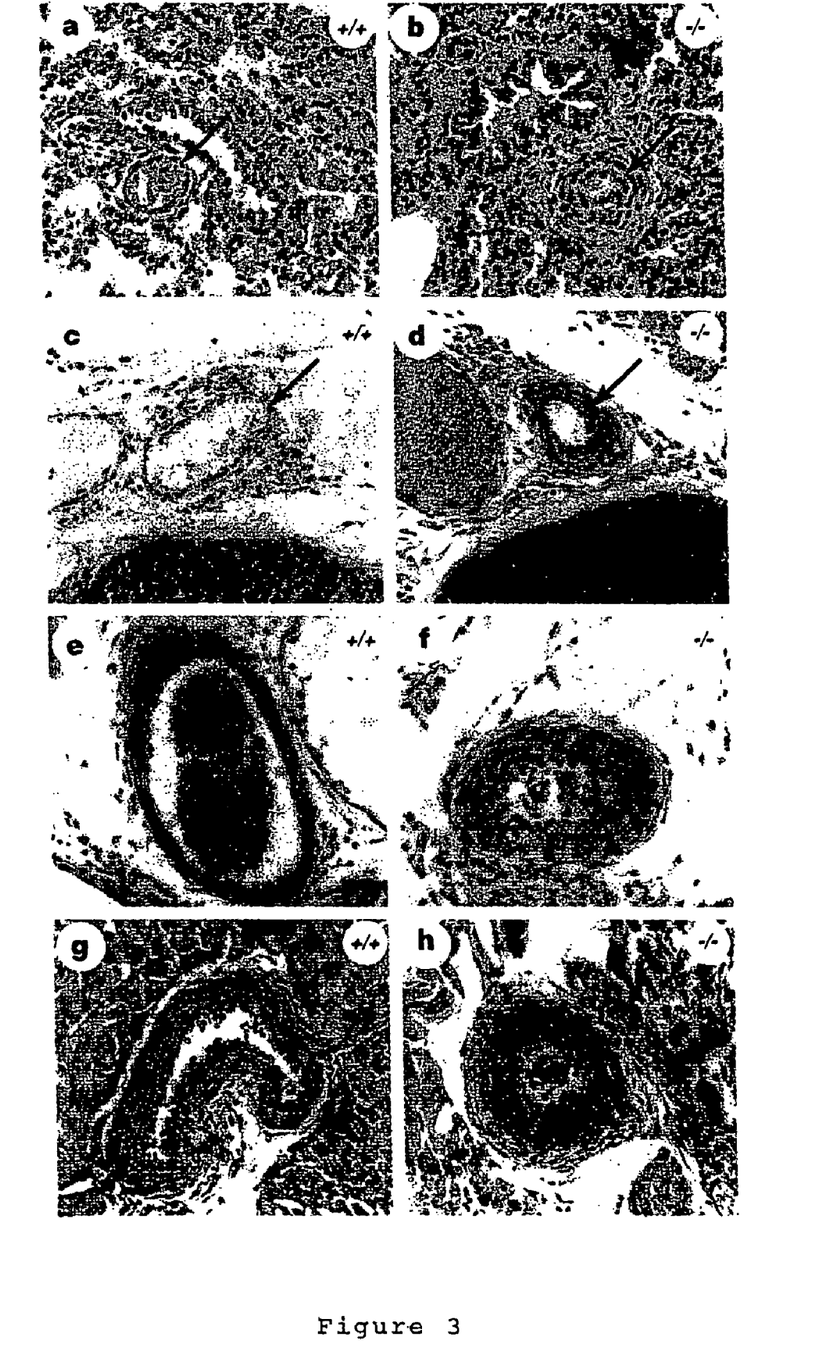

Murine genomic clones encoding elastin (ELN) were isolated from an SV/129λ FIX II library using an ELN cDNA clone. A targeting vector was constructed to delete 4.0 kb of the promoter and exon 1, resulting in a null nutation (FIG. 1A). The vector was electroporated into R1 embryonic stem cells and homologous recombinants were isolated by positive-negative selection (Mansour et al., 1988). Three out of 160 clones were identified as homologous recombinants by Southern analysis (FIG. 1B). These three clones were microinjected into C57BL/6 blastocysts and implanted in pseudopregnant females (Thomas and Capecchi, 1990). All three independent cell lines generated chimeras that transmitted the null ELN allele. The resulting ELN. +/− mice were mated to generate ELN −/− mice.

The disrupted ELN allele is a null as demonstrated by the absence of ELN mRNA and protein in ELN −/− mice (FIGS. 1C-F). Elastin expression during fetal development is largely confined to the vascular system and begins in the last third of gestation (Parks et al., 1993). In situ hybridization demonstrated the absence of ELN mRNA in the aorta of ELN −/− mice and its presence in ELN +/+ and ELN +/− mice (FIGS. 1C-D). Northern analysis showed an absence of ELN mRNA in ELN −/− mice at birth, (0.5 days post partum). Hart staining demonstrated the absence of elastin protein in ELN −/− mice (FIGS. 1E-F).

By contrast with ELN +/+ mice, Northern analysis of ELN +/− mice revealed a 47% decrease in ELN mRNA. To determine if the structure of elastic lamellae in ELN +/− mice was affected, we examined aortic cross sections by electron microscopy. Elastic lamellae in ELN +/− mice were approximately 50% thinner than those in ELN +/+ mice. These data indicate that elastic lamellae in ELN +/− mice are structurally abnormal, presumably due to reduced synthesis of elastin mRNA and protein during development.

B) Changes in Structure and Function of ELN +/− Aortas

ELN +/− mice were identical to ELN +/+ mice in gross appearance, behavior, and life expectancy (Table 1). To determine the effect of ELN hemizygosity on arterial structure, we examined the vascular system using light and electron microscopy. The ascending and descending aorta were examined at 5-14 months. It is generally believed that the number of lamellar units in an artery is fixed, species-specific and genetically determined (Katoh and Periasamy, 1996; Wolinsky and Glagov, 1967). We discovered, however, that aortas dissected from ELN +/− mice had additional lamellar units. Consistent with previous work (Wolinsky and Glagov, 1967; Davis, 1995), we found that ELN+/+ aortas had 5.4±0.5 and 8.4±0.5 layers of elastic lamellae, respectively, in the descending and ascending aorta (Table 2). By contrast, cross sections of ELN +/− mice revealed an increase in the number of lamellar units to 7.3±0.6 and 10.5±0.5 layers, respectively (p<0.005). This represented an increase of 35% and 25% for the descending and ascending aorta of ELN +/− mice. There were no histological differences identified in the cardiac, pulmonary, gastrointestinal, renal, endocrine, musculoskeletal, or integumentary systems. Our results indicate that ELN +/− mice develop aortas with an increased number of elastic lamellae.

To determine the physiological consequences of structural changes observed in ELN +/− mice, we measured aortic diameter and extensibility at varying intraluminal pressures. At a physiological pressure of 100 mm Hg, diameter and extensibility of ELN +/+ and ELN +/− mice were similar. At 125 mm Hg and above, however, the pressure-diameter curves diverged with a marked reduction in extensibility of ELN +/− aortas (p<0.05). These data indicate that ELN+/− mice maintain aortic diameter and extensibility at physiological pressure.

C) ELN +/− Mice Predict SVAS Pathology

SVAS is a human obstructive arterial disease that results from ELN hemizygosity (Ewart et al., 1993). To determine if developmental changes observed in ELN +/− mice were also present in SVAS, we examined aortic segments from affected individuals (n=2 for affected, n=3 for controls). We studied regions of the aorta that were free of discrete stenosis. The number of lamellar units in controls was consistent with previous reports (Machii and Becker, 1997). By contrast, the aortic wall of individuals with SVAS was thicker and contained 2.5 fold more lamellar units (152±27.6 vs. 62±8.7, p<0.025). These data indicated that humans with ELN

TABLE 1

Life Expectancy of ELN +/+, ELN +/−, and ELN −/− Mice

|  | +/+ | +/− | −/− |
|---|---|---|---|
| Embryonic |  |  |  |
| (E15.5-18.5) | 97 (28%) | 163 (48%) | 82 (24%) |
| Postnatal |  |  |  |
| P0.5 | 94 (29%) | 152 (46%) | 81 (25%) |
| P1.5 | 19 (24%) | 45 (57%) | 15 (19%) |
| P2.5 | 33 (26%) | 74 (59%) | 19 (15%) |
| P3.5 | 10 (48%) | 10 (48%) | 1 (4%) |
| >P3.5 | 65 (31%) | 140 (69%) | 0 (0%) |

Litters of mice were sacrificed at each timepoint and genotypes were tabulated. Percentages are calculated in the parenthesis. No ELN −/− mice were alive after P3.5.

TABLE 2

Number of Lamellar Units in ELN +/+ and ELN +/− Aortas

| Mouse ID | Genotype | Age | Ascending | Descending |
|---|---|---|---|---|
| BL6 | WT | 5 mo | 9 | 6 |
| 390-3 | WT | 12 mo | 8 | 5 |
| 390-10 | WT | 14 mo | 8 | 6 |
| 390-11 | WT | 14 mo | 8 | 5 |
| 1002-7 | WT | 4 mo | 9 | 6 |
| 1029-8 | WT | 5 mo | 8 | 5 |
| 1045-3 | WT | 5 mo | 9 | 5 |
|  |  | Average: | 8.4 ± 0.5 | 5.4 ± 0.5 |
| 390-6 | HET | 12 mo | 11 | 7 |
| 390-8 | HET | 14 mo | 11 | 7 |
| 390-9 | HET | 14 mo | 11 | 7 |
| 705-7 | HET | 7 mo | 11 | 8 |
| 720-2 | HET | 7 mo | 10 | 8 |
| 720-6 | HET | 7 mo | 10 | 6 |
| 1029-4 | HET | 6 mo | 11 | 8 |
| 1029-5 | HET | 6 mo | 10 | 7 |
| 1029-6 | HET | 5 mo | 10 | 7 |
| 1029-7 | HET | 5 mo | 10 | 7 |
| 1045-1 | HET | 6 mo | 11 | 7 |
| 1045-4 | HET | 6 mo | 10 | 8 |
|  |  | Average: | 10.5 ± 0.5 | 7.3 ± 0.6 |

Differences in number of lamellar units between ELN +/− mice and ELN +/+ mice were statistically significant with a p<0.005.

hemizygosity, like their murine counterpart, develop an increased number of aortic elastic lamellae.

D) Arterial Occlusion in ELN −/− Mice

ELN −/− mice survived gestation but died by P4.5 (Table 1). To determine the consequences of elastin deficiency, we performed a developmental survey (FIGS. 2A-H). The histological appearance of ascending aortas from ELN −/− and ELN +/+ mice were indistinguishable through embryonic day 17.5 (E17.5). Beginning at E17.5, the outer and inner aortic diameter of the ELN −/− mice became progressively smaller. In ELN +/+ mice, by contrast, the aorta continued to expand. The diameter of the arterial wall in ELN −/− mice became progressively thicker after E17.5. This change was caused by the subendothelial accumulation of cells, a process that eventually obliterated the vascular lumen. Cell counts of the ascending aorta demonstrated a significant difference between ELN +/+ and ELN −/− mice at E17.5 (P<0.025; n=5). By P2.5 there were 76% more cells. in aortic cross-sections of the ELN −/− aortas (P<0.005; n=5).

The aorta and other large, conduit arteries are often referred to as elastic arteries because of the high elastin content and the highly organized structure of elastic lamella (Bloom and Fawcett, 1975). In distributing or muscular arteries, however, the relative proportion of elastin declines and the structure of elastic fibers in the medium is less defined. To determine the consequences of elastin deficiency in different arteries, we examined a pulmonary arteriole, the internal mammary artery, a distal portion of the subclavian artery, and the abdominal aorta in ELN +/+ and ELN −/− mice (FIGS. 3A-H). We found increased cellularity and reduced luminal diameter in systemic and pulmonary arteries of all sizes, including distributing arteries and arterioles (including the descending thoracic aorta, pulmonary, brachiocephalic and carotid arteries) (FIGS. 3A-D). These data indicate that development of several different arteries is abnormal in mice lacking elastin.

Figure 4:
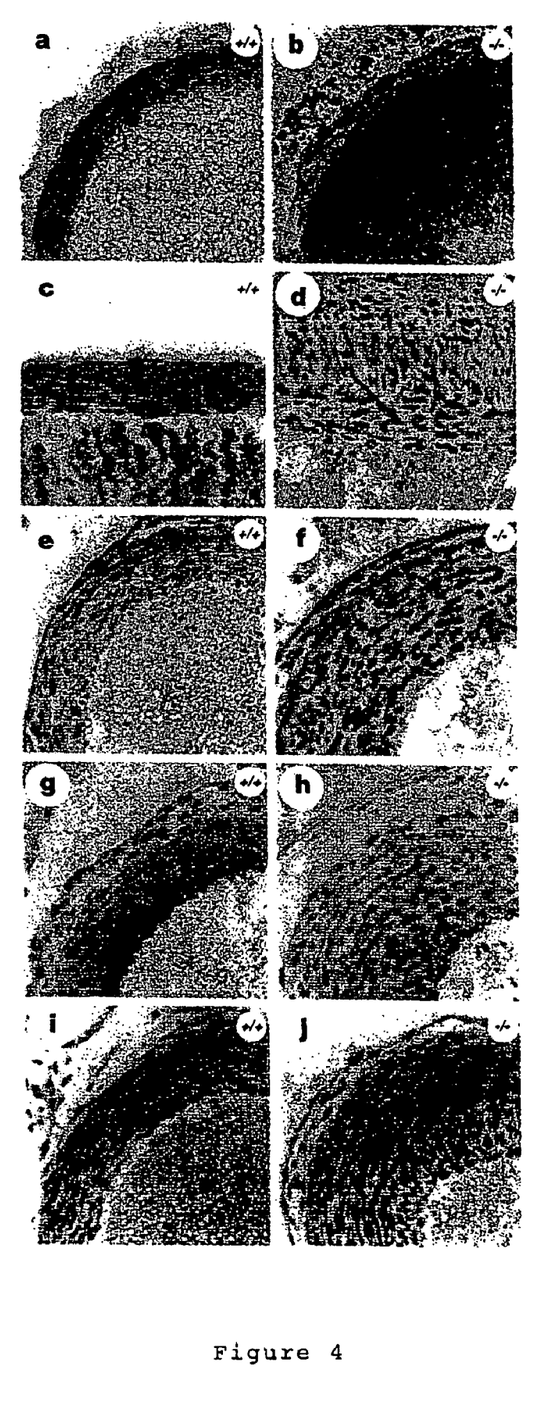
Figure 5:
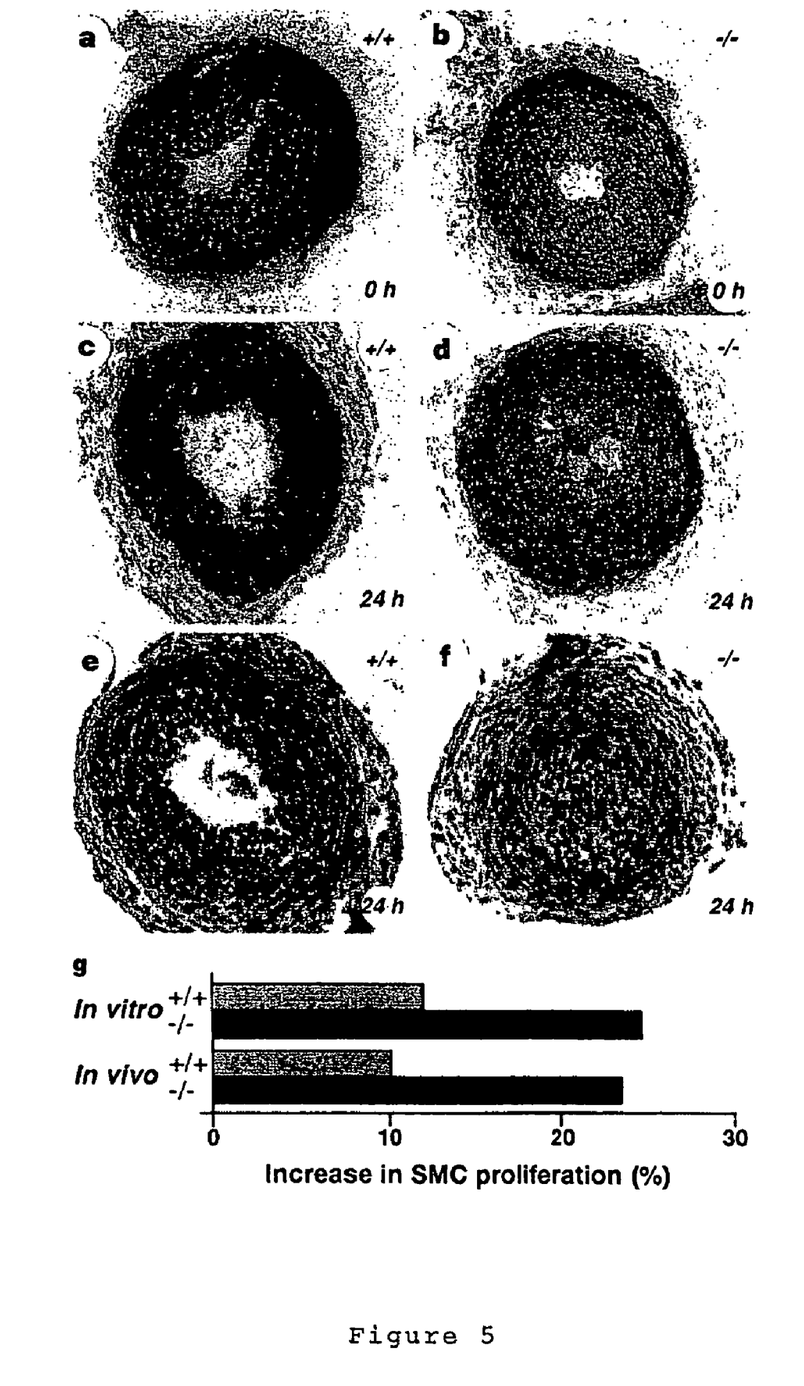

The accumulating cells in aortic cross sections of ELN −/− mice were morphologically distinct from smooth muscle in normal arteries. To determine the identity of these cells, we immunostained aortic sections with antisera against smooth muscle α-actin. The accumulating subendothelial cells present in ELN −/− aortas were positively stained (FIGS. 4A-B). Sagittal sections demonstrated that these cells were longitudinally oriented (FIGS. 4C-D). By contrast, smooth muscle cells in the media of control animals were circumferentially oriented. Thus, luminal obliteration in ELN −/− aortas results from subendothelial accumulation and reorientation of smooth muscle.

To examine the mechanism underlying smooth muscle accumulation in ELN −/− mice, we stained aortic sections with antisera to proliferating-cell nuclear antigen (PCNA; FIGS. 4E-F). At E17.5, the number of cells staining positive for PCNA was greater in ELN −/− mice than in ELN+/+ mice (88% vs. 35%). There was a gradient of staining, with subendothelial cells of ELN −/− aortas staining prominently. Intestinal sections were used as controls, confirming that PCNA was present in the crypts and absent in the villi. These experiments indicate that subendothelial proliferation of smooth muscle is a mechanism underlying the arterial pathology observed in ELN −/− mice.

E) Arterial Obliteration without Inflammation

The hallmark of obstructive arterial disease is subendothelial accumulation of smooth muscle cells (Ross, 1993; Schwartz et al., 1995). It is generally believed that recurrent endothelial injury, thrombosis, and inflammation induce this pathology (Ross, 1993). To determine if these processes were responsible for smooth muscle accumulation in ELN –/– aortas, we used histochemistry, immunohistochemistry, and electron microscopy to examine aortic sections. Sagittal and cross sections of aortas stained with antisera against smooth muscle α-actin revealed a single uninterrupted layer of unstained cells, the endothelium. The identity of these cells was further defined using antisera against von Willebrand factor (FIGS. 4G-H). No evidence of endothelial damage or disruption was observed. Microscopic examination of ELN –/– aortas stained with hematoxylin and eosin showed no evidence of inflammation, there was no ultrastructural evidence of rounding, protrusions, detachment or apoptosis of endothelial cells. Gross and histological examination of arteries revealed no evidence of thrombosis. These results, however, cannot exclude the possibility of endothelial dysfunction.

To determine whether inflammation was responsible for cellular pathology in ELN–/– aortae, we examined sections with hematoxylin and eosin (FIGS. 2A-H and 3A-H). There was no inflammation. Immunohistochemical analyses using the leukocyte-specific antibody Mac-3 also failed to show inflammation. Gross and histological examination of arteries showed no evidence of thrombosis. Because collagen is a ligand for integrin receptors and can modulate proliferation of smooth muscle, we looked for increased collagen levels using Masson trichrome (Koyama et al., 1996). No increase was found (FIGS. 4I-J). Electron micrographs confirmed the integrity of the endothelium, the lack of inflammation and normal distribution of other extracellular matrix proteins, including collagen. Thus, endothelial damage, thrombosis, inflammation, and fibrosis are not responsible for subendothelial accumulation of smooth muscle in ELN –/– mice and, therefore, are not necessary for inducing these pathological changes. Instead, ELN disruption is sufficient for initiating subendothelial accumulation and reorganization of smooth muscle.

Hypertension and hemodynamic stress are important mediators of obstructive arterial disease (Langille and Ojhu, 1997). To determine whether stress to the aortic walls was responsible for increased cell proliferation in ELN –/– aortas, we took aortic segments from ELN +/+ and ELN –/– embryos at E16.5 and incubated them in organ culture (FIGS. 5A-G). In this system, there was no blood flow and no hemodynamic stress. Luminal obliteration by proliferating smooth-muscle cells occurred in ELN –/– mice within 24 hours, but not in ELN +/+ mice. The proliferative index for ELN aortas in organ culture was markedly increased compared with controls (27% vs. 14%; n=8). These indices were similar to those seen for ELN –/– and ELN +/+ aortas between E15.5 and E17.5 in vivo (25% versus 10%; n=5). Thus, blood flow, hemodynamic stress, gross endothelial damage, thrombosis, inflammation, and fibrosis are not responsible for subendothelial accumulation of smooth muscle in ELN –/– mice and therefore are not necessary for inducing these pathological changes. Instead, ELN disruption is enough to initiate accumulation and reorganization of smooth muscle. Therefore endothelial injury, thrombosis, and inflammation contribute to obstructive arterial pathology by disrupting elastin.

F) Physiological Regulation of Arterial Development

It was previously thought that the number of lamellar units in an arterial wall was fixed, species-specific and genetically determined (Katoh and Periasamy, 1996; Wolinsky and Glagov, 1967). Our data are not consistent with this view. We found that ELN +/– mice develop arteries with a marked increase in the number of lamellar units. Examination of arterial specimens obtained from individuals with SVAS, a human disorder caused by ELN hemizygosity, also revealed a dramatic increase in the number of elastic lamellae. Thus, the number of lamellar units in an arterial wall is not fixed or species-specific, but is modulated during development by elastin.

The mechanism underlying elastin's effect on lamellar development is unknown, but likely involves elastin content and wall stress. We found that the increased number of lamellar units observed in ELN +/– mice was associated with reduced ELN mRNA and thinning of each elastic lamella. It is likely that a quantitative reduction in elastin during arterial development resulted in lamellae with reduced extensibility. These changes would lead to increased arterial wall stress, which is determined by arterial pressure and diameter and inversely proportional to the number of lamellar units and the tensile strength of each unit (Milnor, 1990). However, the extensibility and diameter of ELN +/– arteries were normal at physiological pressures. Thus, mice with abnormal elastic fibers maintain arterial extensibility by increasing the number of lamellar units during development. The alternative explanation, that elastin specifies the number of lamellar units by regulating gene expression during arterial development, is unlikely given the extracellular location of elastin. Our model is also supported by physiological studies showing that the relationship between wall stress and the number of elastic lamellae in an artery is remarkably constant despite enormous variation in arterial diameter and stress across species (Wolinsky and Glagov, 1967). We conclude that the number of lamellar units in an arterial wall is modulated daring development by the quantity of elastin and the physiological force of wall stress.

Our work defines a novel pathology in a human obstructive arterial disease, supravalvular aortic stenosis (Perou, 1961; O'Connor et al., 1985). Because of arterial pathology in ELN +/– mice, we reexamined apparently unaffected aortic sections from individuals with SVAS. We discovered a dramatic increase in the number of elastic lamellae. Thus, humans also respond to reduced elastin content by increasing the number of lamellar units during development. The change in humans (150% increase) was more dramatic than mice (25-35% increase), reflecting large differences in wall stress between these species (110,000 versus 7,800 dynes/cm). We could not examine extensibility in humans with SVAS, but progressive arterial pathology in affected individuals suggests that compensatory changes are inadequate, leading to discrete stenoses.

G) Elastin Defines a Fourth Stage of Vasculogenesis

Our studies of ELN –/– mice define a novel stage of vasculogenesis. The results indicate a regulatory function for elastin and define a fourth stage of arterial development. In this fourth and final stage, the extracellular matrix matures, smooth muscle cells exit the cell cycle and become organized, and the artery stabilizes (Hanahan, 1997; Folkman and D'Amore, 1996; Schwartz et al., 1990; Owens, 1995). Arterial development in mice lacking elastin was indistinguishable from controls until E17.5, indicating that elastin has little or no effect on the first three stages of vasculogenesis (Folkman and D'Amore, 1996). During subsequent development, however, ELN −/− aortas became smaller and thicker, arterial diameter declined and the arterial lumen eventually obliterated. The cellular mechanism underlying these changes was subendothelial accumulation of arterial smooth muscle, a process that involved cell proliferation, migration, reorganization and reorientation. Thus, elastin is a molecular determinant of late arterial morphogenesis, stabilizing arterial structure by controlling proliferation and organization of vascular smooth muscle.

By contrast with the mechanism of pathology in ELN +/− mice, it is unlikely that wall stress has an important role in arterial obliteration in ELN −/− mice. As noted above, wall stress is directly proportional to arterial pressure and luminal diameter and inversely proportional to wall thickness. As wall thickness increases and luminal diameter decreases, wall stress declines and approaches zero. Thus wall stress cannot account for luminal obliteration in ELN −/− mice.

The molecular mechanism through which disruption of elastin leads to proliferation and reorganization of arterial smooth muscle is unknown. One likely mechanism is that elastin provides morphogenic signals during arterial development by binding to receptors on the surface of cells. Direct evidence supporting this hypothesis includes ultrastructural data showing specific contact points between smooth muscle cells and elastic lamella, cell biological data demonstrating the ability of elastin peptides to modulate cellular function, and biochemical data identifying an elastin receptor (Davis, 1993; Senior et al., 1984; Mecham and Hinek, 1996). Precedence for this model is provided by the integrin family of receptors that regulate cellular proliferation, migration, differentiation, and organization by binding to fibronectin and other extracellular matrix proteins (Adams and Watt, 1993; Hynes, 1994). A second possible mechanism is that elastin acts by providing a structural cage, directly preventing smooth muscle from proliferating and migrating.

H) Elastin Disruption and Vascular Disease

Obstructive arterial diseases, such as atherosclerosis and restenosis, are the main cause of morbidity and mortality in industrialized nations (American Heart Association, 1996). Although much is known about vascular risk factors like hypercholesterolemia, hypertension, diabetes, and cigarette abuse, the pathogenic mechanism through which these diverse factors converge to give a common pathology is unknown (Schwartz et al., 1995; Gibbons and Dzau, 1996). The hallmark of obstructive arterial disease is subendothelial accumulation of smooth muscle cells, pathology that causes luminal narrowing and life-threatening sequelae (Gibbons and Dzau, 1996; Ross, 1993; Schwartz et al., 1995). Previous models have focused on endothelial injury, thrombosis and inflammation, processes that are thought to induce cellular accumulation through a complex interplay of cytokines and growth factors (Ross, 1993). By contrast with these models, we found no evidence of endothelial damage, thrombosis or inflammation in ELN −/− mice. Instead, we discovered that disruption of ELN is sufficient for inducing smooth muscle proliferation and reorganization. Although disruption of extracellular matrix is a prominent feature of atherosclerosis, this process was not thought central to pathogenesis (Glagov et al., 1987; Galis et al., 1994). Therefore endothelial injury, thrombosis, inflammation, and other vascular risk factors induce subendothelial pathology by disrupting elastin and elastin is central to the pathogenesis of obstructive arterial disease.

I) Drug Screening

Drugs which would either increase the amount of elastin production in a heterozygote for the elastin gene (i.e., ELN +/−) or drugs which would inhibit the uncontrolled growth of subendothelial cells in a homozygote for elastin (ELN −/−) would be beneficial in treating persons with these conditions. Drug screening for such drugs can be performed either in vitro or in vivo.

To promote the amount of elastin production in ELN +/− mice, drugs which promote either transcription, translation or processing of the elastin gene or protein would be desired. Assays to study transcription can be performed in vitro using a purified elastin gene in a vector and including the regulatory regions of the elastin gene. Such a system can also be used to prepare RNA to be used in a cell free translation system to study the effects of drugs on the translation of elastin RNA. Any drugs which promote (i.e., increase) the expression of elastin RNA or the translation of elastin or even the posttranslational processing of elastin are drug candidates for treating persons who are hemizygous or null for functional elastin genes. Such studies can be performed with either human or mouse genes. These studies can be performed by transfecting eukaryotic cells with the elastin gene or they can be performed by taking mouse or human cells and studying the effect on transcription, translation and posttranslational processing of the elastin gene and elastin gene product in the presence and absence of test drugs. Furthermore, such assays can be performed in whole animals. Elastin RNA expression can be measured in any of the above systems (i.e., cell free, transfected cell, mouse or human cell, or whole animal) by hybridization with nucleic acid probes which bind specifically to elastin RNA under the specified hybridization conditions. The elastin gene product can be quantified by means such as measurement with antibodies specific for elastin.

Drug screening need not be performed by evaluating changes at the molecular level, rather screening can be performed by anatomical evaluation or by measuring length of life, especially for mice which are ELN −/−. Mice can be treated with drugs either beginning at birth or preferably before birth. Not all drugs will be accessible to developing embryos in utero, but those drugs which do cross the placenta can be tested by administering drug to the pregnant mother. In the absence of drug, all mice which are ELN −/− die within four days of birth. Screening drugs with such mice can be as simple as crossing heterozygotes to produce the null mice, treating with drug either at or prior to birth, and determining whether any of the mice which survive longer than 4 days are ELN −/−. When such mice are found, the administered drug is a drug candidate for further testing or as a model from which to design related drugs.

Rather than observing life span, mice can be treated with test drugs and the degree of occlusion in the aortas can be examined. For ELN +/− mice this will be enhanced by either causing the mice to become hypertensive or using a strain of mouse which is hypertensive. Drugs which result in mice with less occlusion of their aortas as compared to control mice which were not given drugs are candidate drugs for further testing or as models from which to design related drugs. An alternative assay is to examine the thickness of each lamellar layer in the aortas. Drugs which increase the thickness of each layer as compared to control heterozygous mice not administered drugs are drugs which are candidates for further testing or as models from which to design related drugs.

Following identification of a substance which modulates or affects an activity as described above, the substance may be investigated further. Furthermore, it may be manufactured and/or used in preparation, i.e., manufacture or formulation, or a composition such as a medicament, pharmaceutical composition or drug. These may be administered to individuals. Furthermore, such drugs can be coated onto stents which are to be inserted in a blood vessel such as an artery. Such drug-coated stents will inhibit vascular smooth muscle cell proliferation and migration and can be used to treat or prevent atherosclerosis, transplant arteriopathy or restenosis.

The drugs referred to can be of any type, including but not limited to, nucleic acid, polypeptide or other organic molecule. The present invention extends in various aspects not only to a substance identified as a modulator or promoter of activity as disclosed herein, but also to a pharmaceutical composition, medicament, drug or other composition comprising such a substance, a method comprising administration of such a composition comprising such a substance, a method comprising administration of such a composition to a patient, e.g., for treatment of SVAS, use of such a substance in the manufacture of a composition for administration, e.g., for treatment of SVAS, and a method of making a pharmaceutical composition comprising admixing such a substance with a pharmaceutically acceptable excipient, vehicle or carrier, and optionally other ingredients.

One class of drugs expected to show activity are those which mimic elastin itself. Such an elastin mimetic can be a peptide or a non-peptide. Non-peptide small molecules are often preferred for many in vivo pharmaceutical uses. Accordingly, a mimetic or mimic of the elastin may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

J. Pharmaceutical Compositions and Routes of Administration

The polypeptides, antibodies, peptides, nucleic acids or other drug compounds of the present invention can be formulated in pharmaceutical compositions, which are prepared according to conventional pharmaceutical compounding techniques. See, for example, *Remington's Pharmaceutical Sciences*, 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences*.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635, designed for implantation in a patient. The vector could be targeted to the specific cells to be treated (e.g., the aortic cells), or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731A and WO 90/07936.

The present invention is further detailed in the following Examples, which are offered by way of illustration and are not intended to limit the invention in any manner. Standard techniques well known in the art or the techniques specifically described below are utilized.

EXAMPLE 1

Construction of Targeting Vector

Two phage from a λ FIX II library (Stratagene, La Jolla, Calif.) encompassing exon 1 and spanning a total of 26 kb were isolated, mapped and subcloned. To construct a targeting vector, we used a 6.5 kb XbaI fragment as the 5' region of homology and a 4.2 kb BamHI-HindIII fragment as the 3' region of homology. Positive selection was provided by a 3.1 kb SacI-ClaI fragment containing the neomycin resistance gene under the control of the RNA polymerase II promoter. These fragments were cloned into the vector TK 1-TK2A which provided two thymidine kinase genes for negative selection (Deng et al., 1993).

EXAMPLE 2

Generation of Mice

Culture, selection of embryonic stem cells, and screening of targeted clones were carried out as previously described (Mansour et al., 1988; Thomas and Capecchi, 1990; Lohler et al., 1984; Dietz and Pyeritz, 1995). The R1 embryonic stem cell line used was derived from strain 129/SV X 129/SVJ. Clones were screened by Southern blot analysis of XbaI digested genomic DNA probed with a 3.0 kb HinDIII-XbaI fragment. Random integration events were excluded using a probe derived from the 3' region of homology. The homologous recombinant clones were injected into blastocysts of C57BL/6J and transferred into uteri of pseudopregnant C57BL/6J females. The resulting chimeric animals were backcrossed to C57BL/6J mice, and heterozygous mutants were identified by genomic Southern blotting of tail DNA. Heterozygous mice were mated for three generations with C57BL/6J mice and brother-sister matings were carried out to generate homozygous mutants.

EXAMPLE 3

Northern Analysis and in Situ Hybridization

Poly A(+) RNA was extracted from the visceral organs of the thorax from P0.5 mice using a Micro-FastTrack Kit (Invitrogen, Carlsbad, Calif.). RNA was electrophoresed on a 1.0% denaturing agarose gel, transferred to Hybond filter (Amersham, Arlington Heights, Ill.), and hybridized with a $^{32}$P-labeled 0.85 kb fragment of mouse ELN cDNA. Filters were rehybridized with a 1.5 kb fragment of human cardiac actin cDNA.

Paraffin-embedded cross-sections were hybridized with specific $^{35}$S-labeled antisense and sense ELN complementary RNA probes. Probes were synthesized from linearized templates using T3 and T7 RNA polymerases. Hybridization and washes were performed as described (Prosser et al., 1989). Sections were exposed to emulsion for several weeks and analyzed using bright- and dark-field microscopy.

EXAMPLE 4

Histological Examination

Mice were fixed overnight in either 4% paraformaldehyde or methyl Carnoys at 4° C. and embedded in paraffin. Transverse sections of the ascending and descending aortas were examined at the point at which the pulmonary artery crosses the ascending aorta posteriorly and bifurcates. Sections were stained with hematoxylin and eosin, Hart, and Masson-trichrome. Lamellar units and cell numbers were counted on two separate occasions by individuals blinded to the genotype. The statistical significance was calculated by comparison of the means using Student's t-test analysis.

EXAMPLE 5

Immunohistochemistry

Tissue samples were immunostained with a monoclonal antibody against smooth muscle α-actin (clone 1A4, 1:400, Sigma Chemical, St. Louis, Mo.), human von Willebrand factor antibody (1:1000, DAKO, Carpinteria, Calif.), or proliferating cell nuclear antigen (PCNA) monoclonal antibody (clone PC10, 3 μg/mL, Calbiochem, San Diego, Calif.).

Biotinylated donkey anti-rabbit antibody (RPN 1004, 1:2000, Amersham) was used as a secondary antibody for von Willebrand factor, and biotinylated goat anti-mouse IgG$_{2a}$ antibody (RPN 1181, 1:100, Amersham) was used as a secondary antibody for smooth muscle α-actin and PCNA. Sections immunostained for smooth muscle α-actin or von Willebrand factor were developed with 3-amino-9-ethylcarbazole chromagen (DAKO) and counterstained with Mayers hematoxylin (Sigma Chemical). Sections immunostained for PCNA were developed in 3,3'-diaminobenzidine chromagen (Vector Laboratories, Burlingame, Calif.) and counterstained with methyl green.

EXAMPLE 6

Vascular Extensibility

The ascending aorta from 5-6 month old mice was cannulated and mounted on the pressure myograph (Boyle, 1995). The vessel was transilluminated under an inverted microscope connected to a CCD camera, allowing the continuous recording of the outer diameter of the vessel. Intravascular pressure was increased from 75 to 175 mm Hg by steps of 25 mm Hg, and arterial diameter was recorded. Extensibility was calculated by the following formula using 100 mm Hg as an example; extensibility=[(diameter at 125 mm Hg−diameter at 75 mm Hg)/diameter at 75 mm Hg)]× 100. Statistical analysis was assessed by a four way ANOVA followed by Least Significance Difference test for post ANOVA paired comparisons.

EXAMPLE 7

Organ Culture

Ascending aortas were dissected from mouse embryos at E16.5 and washed in PBS. Aortas were cultured for 24 hours at 37° C. in 5% fetal bovine serum in DMEM. After 24 hours of culturing, each aorta was fixed in 1 mL methyl Carnoys fixative for 16 hours. ELN +/+ and ELN −/− aortas were selected for processing and embedding in paraffin.

EXAMPLE 8

Electron Microscopy

Ascending thoracic aortas were dissected from mouse pups at birth following cardiac perfusion with 3% glutaraldehyde. Aortic segments were sequentially stained with osmium tetroxide, tannic acid and uranyl acetate, then dehydrated and embedded in Epon (Davis, 1995). Thin sections (60 nm) were counterstained with uranyl acetate and lead citrate and examined on a Jeol 1200 electron microscope.

EXAMPLE 9

Use of ELN −/− Mice to Study Vascular Disease

ELN −/− mice do not produce elastin. These mice develop aortas which become filled with an accumulation of subendothelial cells. The absence of elastin results in the uncontrolled growth of subendothelial cells in aortas and these cells eventually block the aortas. In general the blockage of arteries by atherosclerosis or restenosis, e.g., following surgery to clear a blockage, are a main cause of morbidity and mortality in industrialized nations (American Heart Association, 1996). Model systems allowing for the study of these events are extremely useful.

ELN −/− mice are an excellent model for studying vascular disease. The absence of elastin results in an absence of feedback by elastin and thus loss of regulatory control of subendothelial cells. Because of the extracellular location of elastin, the feedback must be via receptors on the subendothelial cells which interact with elastin. Regulation of subendothelial cell growth can be obtained by drugs which interact with these elastin interacting receptors. Mice which produce no elastin are a perfect model system to screen for drugs which can bind to these elastin interacting receptors and thereby regulate the growth of the subendothelial cells. These mice which produce no elastin will give much cleaner results as compared to identical experiments performed with mice which do produce elastin because in the latter mice the elastin will compete with the drug thereby making the results harder to interpret because the overall effect induced by a drug will be less.

Drugs can be screened by treating newborn ELN −/− mice with the test drugs and examining various criteria such as length of life, occlusion of arteries, etc. For certain drugs it will be possible to treat the pregnant mother with test drugs before the null mutant mice are born, thereby getting the drug to the mice even earlier. Such drugs would have to be capable of reaching the developing embryos in utero. In the absence of drug these mice live only a few days and the aortas become rapidly occluded. Drugs which interact with the elastin receptors on the subendothelial cells thereby inhibiting the uncontrolled growth of the subendothelial cells will result in decreased occlusion of the aortas and increased longevity. Drugs discovered by these assays are candidates for use in treating atherosclerosis and for preventing restenosis in humans. Furthermore, the drugs found to work with mice are candidates as model compounds from which similar compounds can be designed for testing in humans. Finally, such compounds can be used to isolate and characterize the elastin receptor itself, e.g., by binding the compound on a column to prepare an affinity column through which a cell extract can be passed. This and related methods are well known to those of skill in the art.

EXAMPLE 10

Use of ELN +/− Mice to Study Vascular Disease

Mice heterozygous for the elastin gene (ELN +/−) show different effects than mice which are null for the elastin gene (ELN −/−). The mice which are null for elastin have abnormal regulation of subendothelial cells which quickly grow and occlude arteries because of the absence of elastin thereby eliminating the interaction of elastin on receptors which lead to normal, regulated growth of the subendothelial cells. By contrast, mice which are heterozygous for the elastin gene do produce elastin and therefore better regulation of subendothelial cells does occur. Nevertheless, heterozygous mice do produce aortas which are different from aortas produced by wild-type mice. The aortas are composed of layers of lamellae wherein each layer is thinner than in wild-type mice but this is at least partially compensated by the fact that the heterozygous mice produce more layers of lamellae. In these heterozygous mice, wall stress (as opposed to lack of elastin interacting with its receptor as in elastin null mice) induces growth of cells thereby causing occlusion of arteries. Such mice therefore are an excellent model for the study of SVAS and of high blood pressure. Mice heterozygous for the elastin gene can be treated with test drugs and over time the amount of occlusion or stenosis can be observed. Drugs which inhibit or result in less occlusion are useful candidates for testing in humans or as model drugs as a starting point to design related drugs for testing in humans. Such drugs can act by interaction with an elastin receptor thereby regulating growth of subendothelial cells or the mechanism of action can be completely different such as activating the expression of the one good actin gene thereby resulting in enhanced production of elastin RNA and in turn enhanced production of elastin. Measurement of elastin RNA synthesis is easily accomplished by hybridization such as on Northern blots. Such methods are known to those of skill in the art.

EXAMPLE 11

Inhibition of Elastase

The foregoing description and Examples indicate the necessity of the presence of elastin and its presence in normal amounts to prevent the occurrence of vascular disease. Factors other than simply the elastin genotype (+/+, +/−, or −/−) can have an effect on elastin or vascular disease. For instance, a mutated receptor which interacts with elastin could easily result in vascular disease. Similarly, improper regulation of the enzyme elastase which degrades elastin can affect the amount of useful elastin present. Too much or too active elastase can result in a shortage of elastin and lead to symptoms as seen in ELN +/− or even in ELN −/− mice or humans. Drugs which inhibit elastase will reverse this effect. Such drugs will be useful for treating heart disease or vascular disease resulting from the presence of too much elastase. Furthermore, even if elastase is wild-type, inhibiting elastase in mice or humans which are ELN +/− will lead to the presence of higher elastin levels which in turn will lead to a phenotype closer to that seen in mice or humans which are wild-type for the elastin gene. Assays can be performed by mixing drugs with purified elastase and elastin to determine whether the drug inhibits elastase activity. Such assays are widely known by those of skill in the art. Many elastase inhibitors are known and have been published in the prior art.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Adams J C and Watt F M (1993). *Development* 117:1183-1198.
American Heart Association (1996). "Heart and Stroke Facts: 1996 Statistical Supplement" (American Heart Association, Dallas, Tex.)
Beck L and D'Amore P A (1997). *FASEB J.* 11:365-373.
Bloom W and Fawcett D (1975). *A Textbook of Histology* 10th edn, pp. 398-402 (Saunders, Philadelphia).
Boyle W A and Maher G M (1995). *Anesthesiology* 82:221-235.
Carmeliet P, et al. (1996). *Nature* 380:435-439.
Curran M, et al. (1993). *Cell* 73:159-168.
Davis E C (1993). *Lab. Invest.* 68:89-99.
Davis E C (1995). *J. Histochem. Cytochem.* 43:1115-1123.
Deng C, et al. (1993). *Mol. Cell. Biol.* 13:2134-2140.
Dietz H C and Pyeritz R E (1995). *Hum. Mol. Genet.* 4:1799-1809.
Ewart A K, et al. (1993). *Nat. Genet.* 5:11-16.
Ferrara N, et al. (1996). *Nature* 380:439-442.
Folkman J and D'Amore P A (1996). *Cell* 87:1153-1155.
Fong G-H, et al. (1995). *Nature* 376:66-70.
Galis Z S, et al. (1994). *J. Clin. Invest.* 94:2493-2503.
Gardner H, et al. (1996). *Dev. Biol.* 175:301-313.
George E L, et al. (1993). *Development* 119:1079-1091.
Gibbons G H and Dzau V J (1996). *Science* 272:689-693.
Glagov S, et al. (1987). *N. Engl. J. Med.* 316:1371-1375.
Glukhova M A, et al. (1991). *Am. J. Physiol.* 261:78-80.
Gumbiner B M (1996). *Cell* 84:345-357.
Hanahan D (1997). *Science* 277:48-50.
Hynes R O (1992). *Cell* 69:11-25.
Hynes R O (1994). *Curr. Opin. Genet. Dev.* 4:569-574.
Katoh Y and Periasamy M (1996). *Trends Cardiovasc. Med.* 6:100-106.
Koyama H, et al. (1996). *Cell* 87:1069-1078.
Langille B C and Ojhu M (1997). *Trends Cardiovasc. Med.* 7:111-118.
Lindahl P, et al. (1997). *Science* 277:242-245.
Lohler J, et al. (1984). *Cell* 38:597-607.
Machii M and Becker A E (1997). *Ann. Thorac. Surg.* 64:511-515.
Mansour S L, et al. (1988). *Nature* 336:348-352.
Mecham R P and Hinek A (1996). In *The Laminins* (P. Elblom and R. Timpl, eds.; Harwood Academic Publishers).
Milnor W R (1990). In *Principles of Hemodynamics in Cardiovascular Physiology*, Oxford University Press, pp. 184-186.
O'Connor W N, et al. (1985). *Arch. Pathol. Lab. Med.* 109:179-185.
Owens G K (1995). *Physiol. Rev.* 75:487-517.
Parks W C, et al. (1993). *Advances in Molecular and Cell Biology* 6:133-182 (Kleinman H K, ed.; JAI, Greenwich).
Perou M (1961). *Arch. Path.* 71:113-126.
Prosser I W, et al. (1989). *Am. J. Pathol.* 135:1073-1088.
*Remington's Pharmaceutical Sciences*, 18th Ed. (1990, Mack Publishing Co., Easton, Pa.).
Ross R (1993). *Nature* 362:801-809.
Saga Y, et al. (1992). *Genes Dev.* 6:1821-1831.
Sato T N, et al. (1995). *Nature* 376:70-74.
Schwartz S M, et al. (1990). *Physiol. Rev.* 70:1177-1209.
Schwartz S M, et al. (1995). *Circ. Res.* 77:445-465.
Senior R M, et al. (1984). *J. Cell Biol.* 22:870-874.
Shalaby F, et al. (1995). *Nature* 376:62-66.
Suri C, et al. (1996). *Cell* 87:1171-1180.
Terpin T and Roach M R (1987). *Can. J. Physiol. Pharmacol.* 65:395-400.
Thomas K R and Capecchi M R (1990). *Nature* 346:847-850.
Thompson R W (1996). *Curr. Opin. Cardiol.* 11:504-518.
Wolinsky H and Glagov S (1967). *Circ. Res.* 20:99-111.
Yang J T, et al. (1993). *Development* 119:1093-1105.
Yang J T, et al. (1995). *Development* 121:549-560.
Zheng X, et al. (1995). *Proc. Natl. Acad. Sci. USA* 92:12426-12430.
U.S. Patent No. 5,550,050
WO 90/07936
WO 92/19195
WO 94/25503
WO 95/01203
WO 95/05452
WO 96/02286
WO 96/02646
WO 96/40871
WO 96/40959
WO 97/12635
EP 425,731A

What is claimed is:

1. A method to screen for peptide candidates which when coated on stents and inserted into a human are useful for treating or preventing atherosclerosis or transplant arteriopathy or are useful in preventing restenosis, comprising
providing elastin −/− mice, which elastin −/− mice have, in comparison to elastin +/+ mice, increased aortic thickening, decreased arterial diameter, and arterial occlusion;
treating said elastin −/− mice with peptides; and
identifying peptides that inhibit cell proliferation or cell migration in vascular smooth muscle cells of said elastin −/− mice;
wherein peptides which inhibit vascular smooth muscle cell proliferation or vascular smooth muscle cell migration are said peptide candidates.

2. The method of claim 1, wherein said peptide candidates are elastin fragments.

3. The method of claim 1, wherein said mice are prenatal mice.

4. The method of claim 3, wherein said peptides are provided to said prenatal mice in utero.

5. A method to screen for peptide candidates which when coated on stents and inserted into a human are useful for treating or preventing atherosclerosis or transplant arteriopathy or are useful in preventing restenosis, comprising
   providing a culture of mouse elastin –/– vascular smooth muscle cells, which elastin –/– vascular smooth muscle cells are derived from an elastin –/– mouse having arterial occlusion in comparison to an elastin +/+ mouse, which elastin –/– vascular smooth muscle cells have increased cell proliferation in comparison to elastin +/+ vascular smooth muscle cells;
   contacting said elastin –/– vascular smooth muscle cells with peptides;
   identifying peptides that inhibit cell proliferation or cell migration in said elastin –/– vascular smooth muscle cells;
   wherein peptides that inhibit vascular smooth muscle cell proliferation or vascular smooth muscle cell migration are said peptide candidates.

6. The method of claim 5, wherein said peptides are elastin fragments.

* * * * *

UNITED STATES PATENT AND TRADEMARK OFFICE
CERTIFICATE OF CORRECTION

PATENT NO. : 7,301,067 B2  Page 1 of 1
APPLICATION NO. : 11/046006
DATED : November 27, 2007
INVENTOR(S) : Keating et al.

It is certified that error appears in the above-identified patent and that said Letters Patent is hereby corrected as shown below:

In the Claims:

In Claim 2, Column 19, line 1, please delete "peptide candidates" and replace with --peptides--.

Claim 5, Column 19, line 13, please delete the word "derived".

Signed and Sealed this

Twentieth Day of May, 2008

JON W. DUDAS
*Director of the United States Patent and Trademark Office*